United States Patent [19]

Nakamura

[11] Patent Number: 5,151,603
[45] Date of Patent: Sep. 29, 1992

[54] METHOD FOR OPTICAL DETERMINATION OF CONCENTRATION OF SUBSTANCE AND APPARATUS FOR THE DETERMINATION

[75] Inventor: Hideki Nakamura, Fuji, Japan

[73] Assignee: Terumo Kabushiki Kaisha, Tokyo, Japan

[21] Appl. No.: 820,021

[22] Filed: Jan. 13, 1992

Related U.S. Application Data

[63] Continuation of Ser. No. 465,239, Apr. 26, 1990, abandoned.

[30] Foreign Application Priority Data

Sep. 3, 1987 [JP] Japan ................. 62-219021
Sep. 2, 1988 [JP] Japan ............ PCT/JP88/00882

[51] Int. Cl.$^5$ ........................................... G01N 21/64
[52] U.S. Cl. ............................. 250/458.1; 250/459.1; 436/136; 436/172
[58] Field of Search ............... 250/458.1, 461.1, 459.1; 436/136, 172

[56] References Cited

U.S. PATENT DOCUMENTS

Re. 31,879  5/1985  Lubbers et al. .
3,612,866  10/1971  Stevens .
4,025,393   5/1977  Hirschfeld .
4,476,870  10/1984  Peterson et al. ............... 250/458.1
4,861,727   8/1989  Havenstein et al. ............... 422/52

FOREIGN PATENT DOCUMENTS 0259951  3/1988  European Pat. Off. .
WO/83/033-44  10/1983  PCT Int'l Appl. .
2132348  7/1984  United Kingdom .

OTHER PUBLICATIONS

"Luminescence Ratio Indicators for Oxygen", Anal. chem. 1987 vol. 59, 279–283.
European Search Report 88 90 7814.
"Measurement of the Diffusion of Oxygen in Polymers by Phosphorescent Quenching", The Journal of Physical Chemistry, vol. 69, No. 11, Nov. 1965.
"Intracellular Measurement of Oxygen by Quenching of Fluorescence of Phyrenebutyric Acid", Biochim. Biophys. Acta, 279 (1972) 393–397.

Primary Examiner—Carolyn E. Fields
Attorney, Agent, or Firm—Burns, Doane, Swecker & Mathis

[57] ABSTRACT

The optical detection of the concentration of a specific substance in a liquid or a gas by the utilization of the quenching of a phosphor by the specific substance or a substance derived from the specific substance is attained with high accuracy by a method and apparatus which comprises causing the system of determination to induce the presence of a first phosphor (A) quenchable by the specific substance or a substance derived from the specific substance and a second phosphor (B) substantially unquenchable by the specific substance or a substance derived from the specific substance, measuring the light signal corresponding to the intensity ($I'_A$) of emission from the first phosphor (A) and the light signal corresponding to the intensity ($I'_B$) of emission from the second phosphor (B), and calculating the ratio between the light signals thereby offsetting variable factors relative to the intensities of emission. The first phosphor is selected from the group consisting of tris(2,2'-bipyridine) ruthenium (II) complex, tris(1,10'-phenanthroline) ruthenium (II) complex, 1-pyrenebutyric acid and salts thereof, pyrene, aminopyrine, perylene, perylene dibutylate, and 2, 7-dichlorofluorescein. The second phosphor is selected from the group consisting of proflavine sulfate, fluorescein, and eosin.

10 Claims, 2 Drawing Sheets

METHOD FOR OPTICAL DETERMINATION OF CONCENTRATION OF SUBSTANCE AND APPARATUS FOR THE DETERMINATION

This application is a continuation of application Ser. No. 07/465,239, filed Apr. 26, 1990, now abandoned.

TECHNICAL FIELD

This invention relates to a method for optical determination of the concentration of a substance and an apparatus for the determination. More particularly, in the optical determination of the concentration of a specific substance in a liquid or a gas by virtue of the variation caused in the intensity of emission from a phosphor by the specific substance or a substance derived from the specific substance, this invention relates to a method and apparatus which, in effecting the optical determination, secure stable response without being conspicuously affected by variable factors.

BACKGROUND

It is known that the fluorophors and phosphors, namely, the so-called phosphors in the generally term, include those of the kind whose intensity of emission is decreased by certain substances. This phenomenon is called "quenching (reaction)" and a substances which induces this quenching reaction is called a "quencher." Generally, the following formula (which is called "Stern-Volmer-equation") is established between the intensity of emission and the concentration of a quencher.

$$I_o/I = 1 + k_q \cdot \tau_o[Q] \qquad (I)$$

wherein $I_o$ is the intensity of emission in the substantial absence of the quencher, I is the intensity of emission when the concentration of the quencher is [Q], $k_q$ is the rate constant of the quenching reaction, and $\tau_o$ is the life of the emission in the substantial absence of the molecules of the quencher, and the product (=K) of multiplied by is the coefficient of quenching.

In this formula (I), $I_o$, $k_q$, and $\tau_o$ are constants which are fixed by the kinds of a phosphor and a quencher contained in the system and the kind of a substance containing the phosphor. The concentration of the quencher, therefore, can be determined by finding the value of I. Where, $I_o$, $k_q$, and $\tau_o$ are unknown, the practice of finding the intensity of emission when the concentration of the quencher is 0 and using the intensity as $I_o$, finding the intensity of emission when the concentration of the quencher is at a known point and using this intensity as I, plotting the ratio of $I_o/I$ relative to the concentration of the quencher, and finding the inclination of the straight line obtained by the plotting as K (=$k_q \cdot \tau_o$) prior to the determination of the concentration of the quencher is generally in vogue. The various constants mentioned above could be found by the use of a device capable of determining the life of emission. This device, however, has not been popularized because it is intricate and expensive.

Incidentally, the method which determines the concentration of a substance by making use of this phenomenon of quenching has found practical utility in various fields. For example, a device for determining the concentration of oxygen by the utilization of the quenching reaction caused by oxygen on such a phosphor as pyrene (Japanese Patent Publication SHO 59(1984)-24,379 and Japanese Patent Laid-Open SHO 59(1984)-108,958, for example), determination of the diffusion coefficient of oxygen in a macromolecular compound by the utilization of the quenching reaction caused by oxygen on such a phosphor as triphenylene (Journal of Physical Chemistry, Vol. 69, No. 11, page 3,677, 1965), and determination of the intracellular distribution of oxygen by the utilization of the quenching reaction caused by oxygen upon pyrenebutyric acid (Biochem. Biophys. Acta., Vol. 279, page 397, 1972) have been known to the art. Though in the examples cited above, the substances themselves subjected to determination function as quenchers relative to phosphors, it is allowable to use other chemical species as quencher. For example, quenchers may be derived by causing substances subjected to determination to undergo certain chemical reactions (such as, for example, "enzymatic reaction"). The determination of concentration may be carried out by utilizing such a quencher which has been derived by a chemical reaction.

In the known methods described above, the fact that the light emanating from an excitation light source and reaching a photo-detector has a constant intensity at all times and the fact that the variation or loss caused to the light signal of emission in a light transmission system extending from a phosphor through a photo-detector is fixed constitute preconditions for the determination. When such a method is put to actual use as for a protracted service, for example, the light intensity of the excitation light source itself entails a drift. When an optical fiber is used as a light transmission system, the response obtained at all is very unstable because the intensity of the light advancing from the excitation light source to the phosphor and the light signal of emission mentioned above are conspicuously affected by variations in such physical conditions as bends in the optical fiber and fluctiations of the ambient temperature.

In other words, the symbol I in the formula (I) or a modification thereof:

$$I = I_o / \{1 + K[Q]\} \qquad (II)$$

always includes a variable component (hereinafter represented by "v"). The intensity of light actually detected by the photo-detector, therefore, ought to be expressed as $I \times (1 + v)$. It follows that the intensity of emission in the absence of a quencher formed of a substance subjected to determination or a substance derived from the substance similarly includes a variable component and this variable component is detected additionally by the photo-detector. Thus, the intensity I cannot be safely treated as a fixed constant throughout the entire course of determination.

To ensure constancy of the light intensity from the excitation light source, many commercially available spectrofluorometers are configured to offset time-course changes of the intensity of excited light by optically taking out in a fixed proportion of intensity a part of the light emanating from the excitation light source (generally a xenon lamp) before the light reaches a sample chamber holding a fluorescent substance, detecting the light intensity of the separated light with an exclusive photo-detector, and feeding back the electric signal from the photo-detector to the voltage being applied to a photomultiplier serving the purpose of detecting the intensity of emission. Peterson et al., in their invention Japanese Patent Laid-Open SHO 59(1984)-500,896 [PCT/US82/01418] concerning use of a probe for determining concentration of oxygen by utilizing the phenomenon that the fluorescence from perylene dibutylate fixed by adsorption on a porous carrier, recommend use of scattered light from an excitation light source as the reference light for the fluorescence.

What is common to these techniques is the fact that they are directed to offsetting the variation of the intensity of light from the light source itself by determining the intensity of a part of the light from the excitation light source. Though these techniques can cope with the variation of the intensity of light from the light source itself, they give no consideration to other variable components of the intensity of emission and, therefore, are ineffective with respect to errors of determination originating in such variations in the determination of the concentration of a substance by the utilization of the quenching described above. The technique recommended in the invention mentioned above is usable only when the light from the excitation light source is scattered at the position containing the phosphor. It produces absolutely no effect in the configuration incapable of producing the scattering or in the configuration incapable of allowing the scattered light produced at all to be introduced into the path of light leading to the detector. By this technique, even the determination is not attained when the intensity of scattered light is very feeble.

An object of this invention, therefore, is to provide a novel method and apparatus for optical determination of the concentration of a substance. Another object of this invention is to provide a method and apparatus for optical determination of the concentration of a specific substance in a liquid or a gas, which accomplishes the determination in a simple configuration with a high accuracy. Yet another object of this invention is to provide a method and apparatus for optically determining the concentration of a specific substance in a liquid or a gas by utilizing the phenomenon that the intensity of emission from a phosphor is varied by the specific substance or by a substance derived from the specific substance, which method and apparatus attains the determination by securing stable response without being conspicuously affected by variable factors.

DISCLOSURE OF INVENTION

The objects described above are accomplished by a method for optical detection of the concentration of a specific substance in a liquid or a gas by utilizing the quenching of a phosphor by the specific substance or a substance derived from the specific substance, which method is characterized by accomplishing the detection of the concentration of the specific substance by inducing the presence of both a first phosphor (A) quenched by the specific substance or a substance derived from the specific substance and a second phosphor (B) not substantially quenched by the specific substance derived from the specific substance, determining a light signal corresponding to the intensity ($I_A'$) of the emission from the first phosphor (A) and a light signal corresponding the intensity ($I_B'$) of emission from the second phosphor (B), and calculating the ratio between the light signals.

This invention further discloses a method for the optical determination of the concentration of a specific substance, wherein the ratio between the light signal corresponding to the intensity ($I_A'$) of emission from the first phosphor (A) and the light signal corresponding to the intensity ($I_B'$) of emission from the second phosphor (B) is calculated for the purpose of calibration with respect to at least two different known concentration of the specific substance prior to the detection of the concentration of the specific substance. This invention further discloses a method for the optical determination of the concentration of a substance, wherein the emission spectrum of the first phosphor (A) and the emission spectrum of the second phosphor (B) fall in mutually different wavelength regions. This invention further discloses a method for the optical determination of the concentration of a substance, which method is used for the determination of the concentration of oxygen.

The objects described above are accomplished by an apparatus comprising a sensor part formed of a layer containing a phosphor, an excitation light source for exciting the phosphor, a measuring part for detecting the intensity of emission, and a light guiding part for transmitting to the measuring part the light signal corresponding to the emission of the phosphor in the sensor part and effecting the optical determination of the concentration of a specific substance in a liquid or a gas by the utilization of the quenching of the phosphor by the specific substance or a substance derived from the specific substance, which apparatus is characterized by the fact that the sensor part contains at least two phosphors comprising at least one phosphor quenchable by the specific substance or a substance derived from the specific substance and at least one phosphor substantially unquenchable by the specific substance or a substance derived from the specific substance and the measuring part is provided with optical technical means for distinctly detecting the light signals corresponding to the intensities of emission of the phosphors.

This invention further discloses an apparatus for the optical determination of the concentration of a specific substance, wherein the sensor part contains at least two phosphors having emission spectra in mutually different wavelength regions and comprising at least one phosphor quenchable by the specific substance or a substance derived from the specific substance and at least one phosphor substantially unquenchable by the specific substance or a substance derived from the specific substance. This invention further discloses an apparatus for the optical determination of the concentration of a specific substance, wherein the light guiding part serves commonly for the emission of the individual phosphors in the sensor part and the measuring part is provided with a spectroscope for dispersing the light signals guided by the light guiding part into different wavelength components corresponding to the emissions of the phosphors, a photo-detector for converting the light signals in the dispersed wavelength components into electric signals, and an arithmetic device for calculating the ratio between the light signal corresponding to the intensity of emission of the phosphor quenchable by the specific substance or a substance derived from the specific substance and the light signal corresponding to the intensity of emission of the phosphor substantially unquenchable by the specific substance or a substance derived from the specific substance based on the electric signals obtained by the photo-detector.

This invention further discloses an apparatus for the optical determination of the concentration of a specific substance, wherein the sensor part contains in one and the same reagent layer thereof the phosphor quenchable by the specific substance or a substance derived from the specific substance and the phosphor substantially unquenchable by the specific substance or a substance derived from the specific substance. This invention further discloses an apparatus for the optical determination of the concentration of a specific substance, wherein the sensor part contains in mutually different yet adjacent reagent layers thereof the phosphor quenchable by the specific substance or a substance derived from the specific substance and the phosphor substantially unquenchable by the specific substance or a substance derived from the specific substance.

BEST MODE FOR CARRYING OUT THE INVENTION

Figure 1:
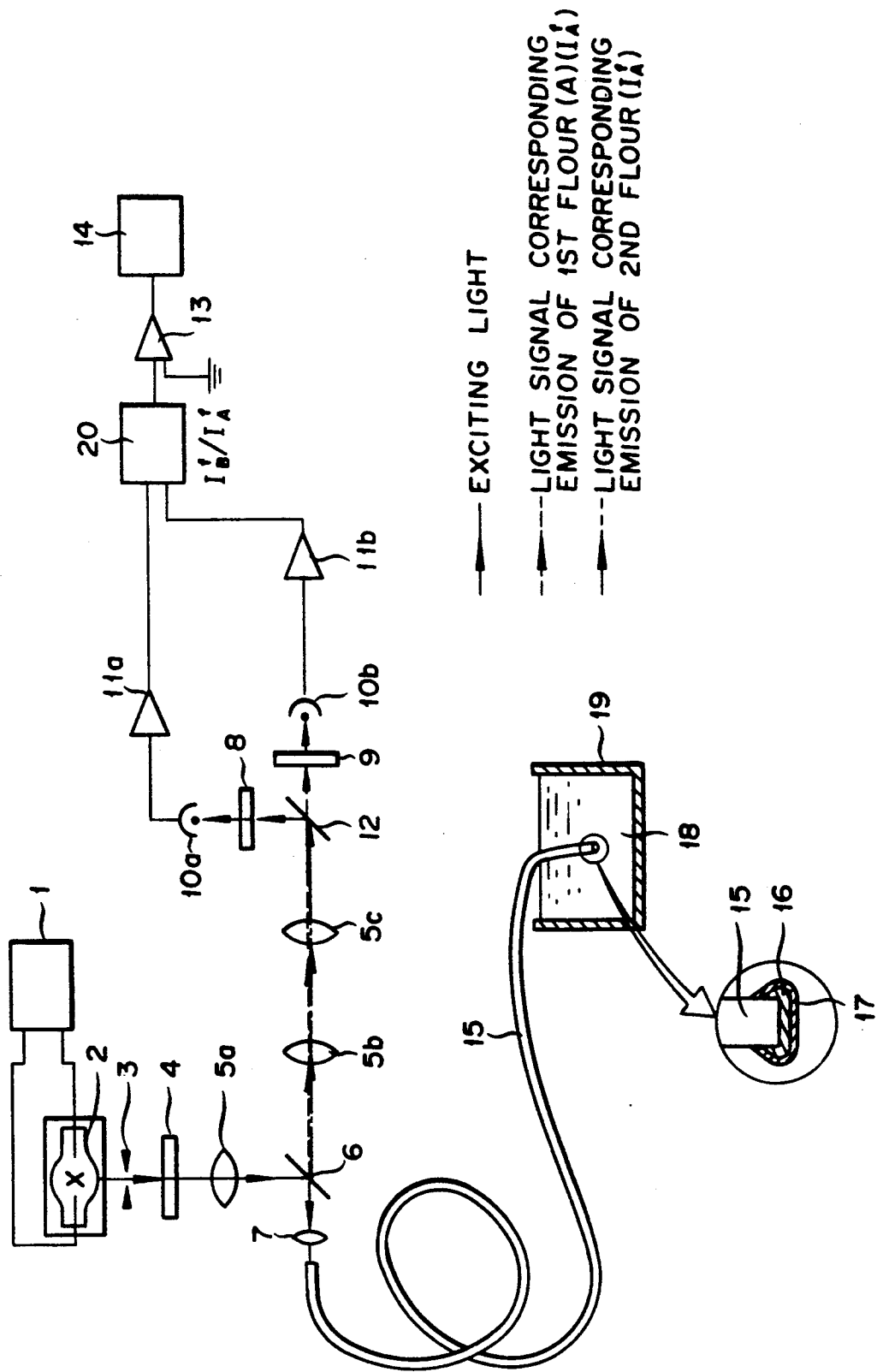
FIG. 1 is a schematic diagram illustrating the configuration of a typical apparatus for the determination of the concentration of a substance as one embodiment of this invention and FIG. 2 is a graph showing the relation between the partial pressure of oxygen and the ratio of $I_B{}^f/I_A{}^f$.

This invention is directed to a method for optical detection of the concentration of a specific substance in a liquid or a gas by utilizing the quenching of a phosphor by the specific substance or a substance derived from the specific substance, which method is characterized by accomplishing the detection of the concentration of the specific substance by inducing the presence of both a first phosphor (A) quenched by the specific substance or a substance derived from the specific substance and a second phosphor (B) not substantially quenched by the specific substance or a substance derived from the specific substance, determining a light signal corresponding to the intensity ($I_A{}^f$) of the emission from the first phosphor (A) and a light signal corresponding the intensity ($I_B{}^f$) of emission from the second phosphor (B), and calculating the ratio between the light signals.

The inventors continued a diligent study in search of a technique for eliminating the influences of variable factors from the light signal corresponding to the intensity of emission from a phosphor subjected to detection. They have consequently drawn a conclusion that the determination of the concentration of the specific substance is attained with high accuracy based on the following theory by inducing within the system of determination the presence of a phosphor [first phosphor (A)] quenchable by a quencher (the specific substance or a substance derived from the specific substance) and a phosphor [second phosphor (B)] substantially unquenchable by the quencher. In the Stern-Volmer equation (II) indicating the relation between the intensity of emission and the quencher, when the variable component "v" mentioned above is taken into account, the first phosphor (A) and the second phosphor (B) which are present in the system of determination are represented respectively as follows.

$$I_A{}^f = I_{A,o}{}^f(1+v)/\{1+K[Q]\} \quad (III)$$

$$I_B{}^f = I_{B,o}{}^f(1+v) \quad (IV)$$

In the formula (III) and the formula (IV), the suffix "f" denotes a light signal actually determined with the light detecting element and the suffix "O" denotes the intensity of emission occurring in the absence of a quencher formed of a substance subjected to determination or a substance derived from the substance just mentioned. The symbols, $I_A{}^f$ and $I_B{}^f$ denote the light signals actually detected by the photo-detector when the light emitted from the first phosphor (A) and the light emitted from the second phosphor (B) are led by the existing optical technique to the photo-detector. These light signals represent the intensities of emission from the first phosphor (A) and the second phosphor (B), as deformed by incorporation therein of such variable components as variation of the intensity of light from the light source and loss of the light intensity in the light guiding part, for example. Since the emission of the second phosphor (B) is not quenched even in the presence of a quencher, the quenching coefficient K relative to the intensity of emission of the second phosphor (B) is substantially 0. Hence, the formula (IV) is established.

In the configuration which allows the presence of both the first phosphor (A) and the second phosphor (B) within the system of determination and equalizes the variable components of the respective emissions, the following formula of relation is derived from the formula (III) and the formula (IV).

$$I_B{}^f/I_A{}^f = (I_{B,o}{}^f/I_{A,o}{}^f) \times \{1 + K[Q]\} \quad (V)$$

The formula of relation (V) no longer contains the variable component "v". Since $I_{B,o}{}^f/I_{A,o}{}^f$ and K are constants to be fixed by the particular phosphor to be used, the concentration [Q] of the quencher can be found without being affected by any variable component by detecting $I_B{}^f/I_A{}^f$ (or $I_A{}^f/I_B{}^f$). This method, therefore, enables the determination be obtained stably with high accuracy as compared with the conventional method which determines the concentration [Q] of the quencher by inducing within the system of determination the sole presence of the phosphor [first phosphor (A)] quenchable by the quencher and simply detecting $I_A{}^f$.

Now, the present invention will be described more specifically with reference to embodiments.

The method of this invention for the optical determination of the concentration of a specific substance, similarly to the conventional method for the optical determination of a specific substance, effects the optical detection of the concentration of a specific substance in a liquid or a gas by utilizing the quenching action exerted on the emission of the phosphor by the specific substance or a substance derived from the specific substance. It similarly applied to the various fields to which the conventional method is applied. It is utilized advantageously for the determination of concentrations of NO, and $NO_2$ in the air or for the determination of $O_2$, concentrations of oxygen, nitrogen, hydrogen, carbon dioxide, chlorine, argon and other dissolved gases in water, blood or other similar aqueous media. The substance which is subjected to determination by the method of this invention for the optical determination of the concentration of a specific substance not only the specific substance which manifests the quenching action directly on the emission of the first phosphor (A) of the nature to be described specifically hereinafter (namely the substance under determination serves as the quencher) but also other chemical species derived from the specific substance through a chemical reaction of one sort or other (such as, for example, enzymatic reaction) and possessed of the action to quench the emission of the first phosphor (A) (namely the substance derived from the substance under determination serves as the quencher).

In the method of this invention for the optical determination of the concentration of a specific substance, the first phosphor (A) which is quenchable by the specific substance of the nature described above and subjected to the determination or a substance derived from the specific substance and the second phosphor (B) which is substantially unquenchable by the specific substance of the nature described above or a substance derived from the specific substance are used. The first phosphor (A) and the second phosphor (B) to be used are suitably selected from among those of various phosphors, namely substances capable of generating phosphorescence or phosphorescence on being excited by an exciting light, which fulfil the requirements of the phosphors (the requirement of being quenchable by the quencher with respect to the first phosphor and the requirement of being substantially unquenchable by the quencher with respect to the second phosphor). The first phosphor (A) may be capable of being loosely bound with the quencher to form a non-fluorescent complex and induce static quenching or capable of colliding with the quencher in an excited state to be deprived of the excitation energy and to induce dynamic quenching. The first phosphor (A) and the second phosphor (B) to be used herein are naturally variable with the particular kind of the quencher formed of the substance subjected to determination or a substance derived from the substance. Where the quencher is oxygen, for example, the compounds which are usable as the first phosphor (A) include tris(2,2'-bipyridine) ruthenium (II) complex, tris(1,10'-phenanthroline) ruthenium (II) complex, 1-pyrenebutyric acid and salts thereof, pyrene, aminopyrene, perylene, perylene dibutylate, and 2,7-dichlorofluorescein, for example, and the compounds which are usable as the second phosphor (B) include proflavine sulfate, fluorescein, eosin Y, and many other fluorophors, for example.

The method of this invention for the optical determination of the concentration of a specific substance requires the presence in the system of determination of the first phosphor (A) which is quenchable by the specific substance of the nature described above and subjected to the determination or a substance derived from the specific substance and the second phosphor (B) which is substantially unquenchable by the specific substance or a substance derived from the specific substance. The distinct detection of the light signals, $I_A{}^f$ and $I_B{}^f$ corresponding intensities of emission of the respective phosphors can be attained by any of several methods. A few of these methods are enumerated below.

(1) A method which comprises optically separating different wavelength components by virtue of mutual difference between the emission spectra of the first phosphor (A) and the second phosphor (B) and leading the separated wavelength components to a photo-detector.

(2) Where the emission spectra from the first phosphor (A) and the second phosphor (B) overlap each other in a wide wavelength region and, therefore, cannot be distinctly separated into two different wavelength components by the optical technique, a method which comprises detecting the emissions from the phosphors at mutually independent moments of timing or causing two light signals to be detected one each by two detectors.

(3) A method which comprises calculating the intensities of emission from the first phosphor (A) and the second phosphor (B) by measuring the difference of life between the emissions from the first phosphor (A) and the second phosphor (B) and analyzing the outcome of the measurement.

Though these methods can be invariably executed by the existing optical technique, the method of (1) proves to be most desirable in all of these methods. The method of (2) does not operate unless the first phosphor (A) and the second phosphor (B) are contained one each in two mutually independent reagent layers. Further, it is difficult to equalize the variable components relative to the intensities of emission. The method of (3) inevitably requires use of a special pulse light source (such as, for example, a hydrogen-discharge tube or a laser), a single photo-counting technique, an integrating device, and a computer. Thus, the apparatus for working this method is complicate and the determination consumes a long time. The term "reagent layer" as used herein refers to the position in which the phosphor is contained. Generally, the reagent layer is made of a matrix in which the quencher formed of the substance subjected to determination or a substance derived from the substance under determination is easily diffused.

In the method of this invention for the optical determination of the concentration of a specific substance, the concentration [Q] of the quencher can be obtained by causing the intensities of emission from the first phosphor (A) and the second phosphor (B) to be led by the existing optical technique to the photo-detector, actually detecting the light signals, $I_A{}^f$ and $I_B{}^f$, with the photo-detector, and substituting these light signals in the aforementioned general formula (V):

$$I_B{}^f/I_A{}^f = (I_{B,o}{}^f/I_{A,o}{}^f) \times \{1 + K[Q]\} \qquad (V)$$

Incidentally, the terms, $I_{B,o}{}^f/I_{A,o}{}^f$ and K, in the general formula (V) are constants to be fixed by the particular phosphors to be actually used. They are generally unknown. It is, therefore, preferable to calculate the ratio between the light signal corresponding to the intensity ($I_A{}^f$) of emission from the first phosphor (A) and the light signal corresponding to the intensity ($I_B{}^f$) of emission from the second phosphor (B) relative to at least two different known concentrations and calibrate the unknown concentrations of the specific substance subjected to determination in advance of the determination of the concentration of the specific substance.

The method for effecting the optical determination of the concentration of a specific substance as described above can be executed by an apparatus comprising a sensor part formed of a layer containing a phosphor, an excitation light source for exciting the phosphor, a measuring part for detecting the intensity of emission, and a light guiding part for transmitting to the measuring part the light signal corresponding to the emission of the phosphor in the sensor part and effecting the optical determination of the concentration of a specific substance in a liquid or a gas by the utilization of the quenching of the phosphor by the specific substance or a substance derived from the specific substance, which apparatus is characterized by the fact that the sensor part contains at least two phosphors comprising at least one phosphor quenchable by the specific substance or a substance derived from the specific substance and at least one phosphor substantially unquenchable by the specific substance or a substance derived from the specific substance and the measuring part is provided with optical technical means for distinctly detecting the light signals corresponding to the intensities of emission of the phosphors. Particularly for the reason given above, the method described above can be more advantageously executed by an apparatus for the optical determination of the concentration of a specific substance, wherein the sensor part contains at least two phosphors having emission spectra in mutually different wavelength regions and comprising at least one phosphor quenchable by the specific substance or a substance derived from the specific substance and at least one phosphor substantially unquenchable by the specific substance or a substance derived from the specific substance.

In the apparatus for the optical determination of the concentration of a specific substance described above, it is sufficient for the sensor part thereof to contain one kind each of the first phosphor (A) quenchable by the specific substance or a substance derived from the specific substance and the second phosphor (B) substantially unquenchable by the specific substance or a substance derived from the specific substance. Even when the sensor part contains these phosphors each in a plurality of kinds, the apparatus can be operated safely so long as this apparatus is provided with a measuring part capable of independently detecting the intensities of emission from the individual phosphors contained.

In the sensor part, the first phosphor (A) and the second phosphor (B) are Preferable to be contained in one and the same reagent layer. This is because the common use of one optical system by the two phosphors up to the step of spectral dispersion of the phosphors can be further facilitated the variable components "v" are equalized between the first phosphor (A) and the second phosphor (B).

Optionally, in the sensor part, the first phosphor (A) and the second phosphor (B) may be contained in two mutually different yet adjacent reagent layers. In this case, the two reagent layers may be disposed either parallelly or serially relative to the optical axis. The sensor part containing the two reagent layers, however, is slightly complicated as compared with the sensor part having the first phosphor (A) and the second phosphor (B) contained in one and the same reagent layer.

The excitation light source in the apparatus of this invention for the optical determination of the concentration of a specific substance may be a continuous light or a pulsating light so long as the light source is capable of producing a wavelength fit for exciting the first phosphor (A) and the second phosphor (B). The excitation light sources which are effectively usable herein include a xenon lamp, an ultra-high pressure mercury lamp, a laser, and a light- emitting diode, for example.

As the light guiding part for transmitting the light signal corresponding to the emission of the phosphor to the measuring part, an optical fiber or a varying lens may be used. For the purpose of equalizing the variable component "v" between the first phosphor (A) and the second phosphor (B), the light guiding part is desired to be used commonly in the sensor part for the emission of the first phosphor (A) and the second phosphor (B).

The measuring part for measuring the light signals led by the light guiding part can be easily formed by the conventional optical technique. Where the emission spectrum of the first phosphor (A) and the emission spectrum of the second phosphor (B) fall in different wavelength regions, for example, the measuring part is typically composed of a spectroscope capable of dispersing the emissions of the phosphors into different corresponding wavelength components, a photo-detector for converting the light signals in the dispersed wavelength components into electric signals, and an arithmetic device for calculating the ratio, $I_B{}^f/I_A{}^f$ between the light signal, $I_A{}^f$, corresponding to the intensity of emission of the phosphor [first phosphor (A)] quenchable by the specific substance or a substance derived from the specific substance and the light signal, $I_B{}^f$, corresponding to the intensity of emission of the phosphor [second phosphor (B)] substantially unquenchable by the specific substance or a substance derived from the specific substance in accordance with the electric signal obtained by the aforementioned photo-detector.

As the spectroscope for spectrally dispersing the light signal led by the light guiding part into different wavelength components corresponding to the emissions of the phosphors, any of the spectroscopes based on various methods of spectroscopy such as, for example, (1) the method using such an optical filter as an interference filter or a dichroic mirror, (2) the method which uses a diffraction grating, and (3) the method which uses a prism [described in detail as in "Applied Spectroscopy Handbook," (published by Asakura Shoten)]. In these methods, the method of (1) using an optical filter is least expensive to operate. The apparatus for executing this method is compact in structure. The method of (2) using a diffraction grating proves to be desirable where the spectroscopy is desired to be effected with high sensitivity. Incidentally, the method of (3) using a prism is not fit for popular use because it has its limit in brightness, though the apparatus is simple in structure.

The photo-detector is described in detail in literature and can be suitably selected depending on the wavelength of emission of the phosphor, the intensity of emission, and the like. For the determination of a feeble light in the ultraviolet and visible region including wavelength regions of emission of numerous phosphors, the photomultiplier is used popularly because of the highest sensitivity attainable. Such solid type photo-detectors as a photodiode and a phototransistor are also usable. Where the first phosphor (A) and the second phosphor (B) are present one each in the sensor part, the apparatus of this invention for the optical determination of the concentration of a specific substance may be configured to incorporate two photo-detectors or one photo-detector therein. In the former configuration, the optical system enjoys simplicity of structure because two photo-detectors (one photodiode array suffices because the array itself is a multi-element device) are used for enabling the emission from the individual phosphors to be determined independently of each other. In contrast, in the latter configuration, a light chopper or a rotary mirror is used as employed in many two-beam spectroscopic devices (such as, for example, an ultraviolet visible spectrophotometer) to split the timing of spectral dispersion or to differentiate the timing of introducing the dispersed light into one detector between the two emissions and a lock-in amplifier is used for effecting synchronous amplification. The latter configuration enjoys an advantage that the background current of the photo-detector is offset, though it is complicate in structure.

FIG. 1 is a schematic diagram illustrating the configuration of a typical apparatus for the optical determination of the concentration of a specific substance as one embodiment of the present invention. The apparatus for the optical determination of the concentration of a specific substance illustrated in FIG. 1 is an apparatus for determining the concentration of oxygen dissolved in a liquid. It is provided as an excitation light source with an ultra-high mercury lamp 2 connected to a DC electric power source 1, as a sensor part with a probe formed by covering a permeable membrane 17 capable of selectively passing dissolved oxygen with a reagent layer 16 having uniformly dispersed in one and the same matrix the first phosphor (A) quenchable by oxygen and the second phosphor (B) substantially unquenchable by oxygen, as a light guiding part with an optical fiber 15 used commonly for the emissions in the sensor part, as a measuring part with a spectroscope formed by combining a beam splitter 12 and interference filters 8 and 9 for selectively passing only the portions of the phosphors falling within specific wavelength regions, a photodetector formed of two photomultipliers 10a, 10b for detecting the light signals passing the interference filters 8 and 9 and converting them into electric signals, and an arithmetic device 20 for calculating the ratio of the electric signals obtained by the two photomultipliers 10a, 10b (the ratio between the light signal corresponding to the intensity of emission of the first phosphor (A) and the light signal corresponding to the intensity of emission of the second phosphor (B)).

In this apparatus, the exciting light emitted from the ultra-high mercury lamp 2 is passed through a diaphragm 3 and treated with the interference filter 4 for selective separation of the light of a specific wavelength region. The separated light is converted by a convex lens 5a, brought to a dichromic mirror 6 to be reflected and polarized thereby, converged by an objective lens 7, and inserted into an optical fiber 15. When the excited light guided by the optical fiber 15 reaches the reagent layer 16 placed at the leading end of the optical fiber 15, the first phosphor (A) and the second phosphor (B) contained in the reagent layer 16 are caused to radiate emissions of their own wavelengths. The emissions impinge on the optical fiber 15. The emission of the first phosphor (A) is quenched because dissolved oxygen is present in a reagent solution 19 contained in a water bath 18 and this dissolved oxygen gas permeates a permeable membrane 17 and diffuses in the reagent layer 16. In the meantime, the emission of the second phosphor (B) is not affected by the presence of the dissolved oxygen mentioned above. The emission transmitted through the optical fiber 15 and emitted therefrom is converted by the objective lens, passed through the dichromic mirror 6, again converged by the pair of convex lenses 5b, 5c, divided into two equal light fluxes by a beam splitter 12, and brought to the interference filters 8 and 9. Through the interference filter 8, only the light signal in the wavelength region of the emission of the second phosphor (B). The light signal corresponding to the emission of the second phosphor (B) is detected and converted into electric signal by the photomultiplier 10a. The electric signal is amplified by a preamplifier 11a and forwarded to an arithmetic device 20. Through the interference filter 9, only the light signal in the wavelength region of the emission of the first phosphor (A) is passed. The light signal corresponding to the emission of the first phosphor (A) is detected and converted into an electric signal by the photomultiplier 10b. This electric signal is amplified by the preamplifier 11b and forwarded to the arithmetic device 20. In the arithmetic device 20, the ratio of the electric signals forwarded through the photomultipliers 10a and 10b is calculated. This ratio is amplifier by the amplifier 13 and is recorded or displayed in a recorder or a digital multimeter 14.

Now, this invention will be described more specifically below with reference to a working example. Example Ruthenium (II) tris(2,2'-bipyridine) chloride (produced by Aldrich Corp) was used as the first phosphor (A) quenchable by oxygen and proflavin sulfate (produced by Aldrich Corp) a the second phosphor (B) unquenchable by oxygen.

First, in 1 ml of an aqueous solution containing 5 mM of ruthenium (II) tris(2,2'-bipyridine) chloride and 0.1 mM of proflavin sulfate, 100 mg of polyvinyl pyrrolidone (produced by Wako Junyaku K. K. and marketed under product code of "K-30") was dissolved.

One terminal of a plastic optical fiber (produced by Mitsubishi Rayon Company Limited and marketed under product code of "SH-2001") cut in a length of 2 m was disposed in and pulled out of the aforementioned aqueous solution and dried to obtain a reagent layer (about 0.01 mm in thickness). Then silicone sealant (produced by Toray Silicone K. K. and marketed under product code of "SE-2001") was applied to the reagent layer and allowed to cure, to give rise to an oxygen permeable membrane (about 0.05 mm in thickness). The optical fiber provided with a probe for determination of the concentration of oxygen obtained as described above was set in place in an apparatus for the optical determination of the concentration of a specific substance configured as illustrated in FIG. 1. In the apparatus illustrated in FIG. 1, the maximum permeable wavelength of the interference filter 4 was 435 nm, the maximum permeable wavelength of the interference filter 8 was 610 nm, the maximum permeable wavelength of the interference filter 9 was 510 nm, the focal distance, f, of the convex lenses 5a, 5b, and 5c was 200 mm, and the magnification of the objective lens 7 was 20. Water was placed in the water tank 19 and an oxygen- containing nitrogen gas was blown into the water.

Figure 2:
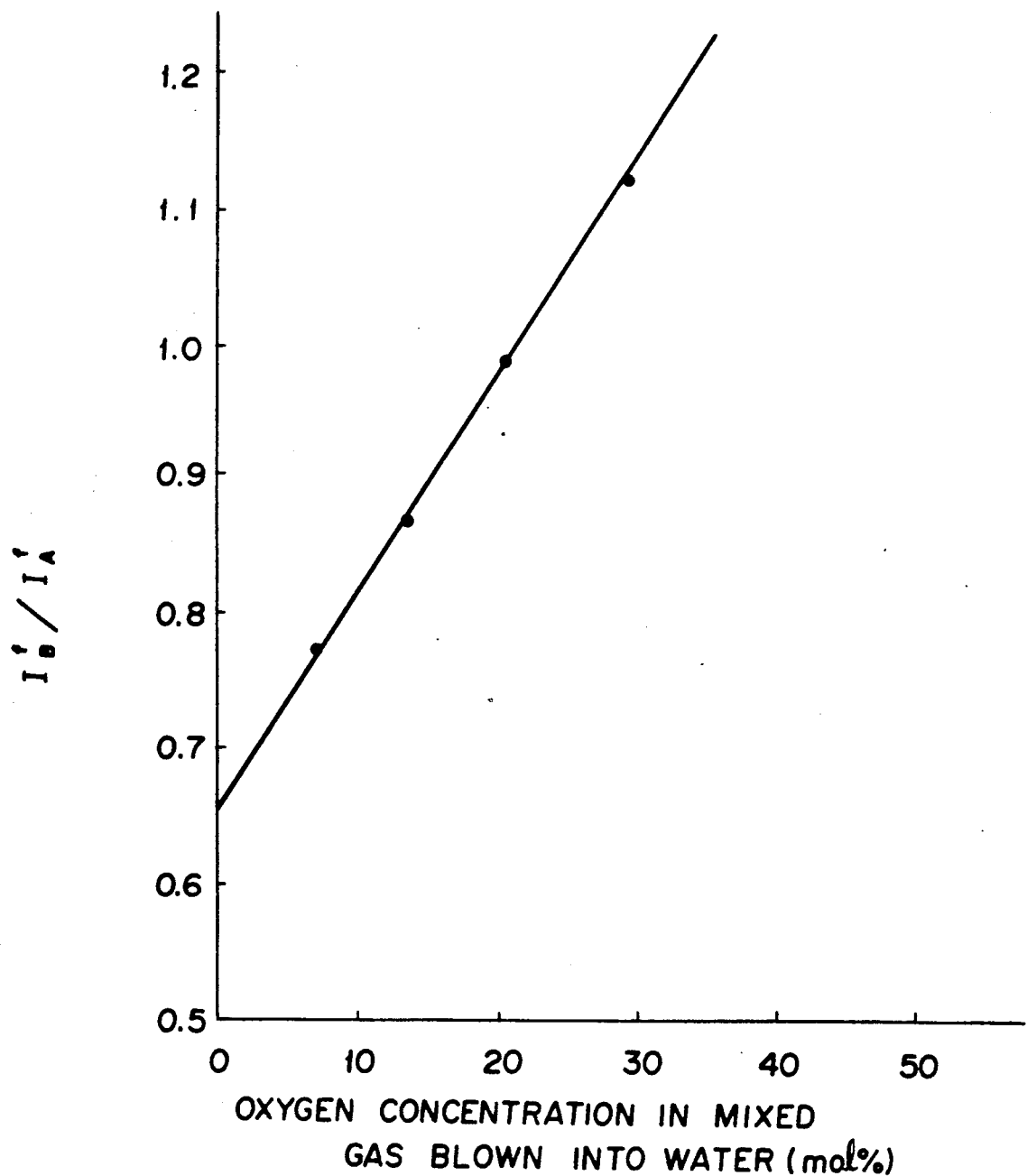

The probe mentioned above was placed in the water and the ratio, $I_B^f/I_A^f$ of the intensities of emission was measured for varying partial pressures of oxygen. The results are shown in Table 1 and FIG. 2.

TABLE 1

| Oxygen concentration in gas introduced into water (mol %) | $I_B^f/I_A^f$ |
|---|---|
| 0 | 0.659 |
| 7.0 | 0.772 |
| 13.4 | 0.867 |
| 20.5 | 0.973 |
| 29.2 | 1.104 |

As shown in Table 1, a satisfactory linear relation was obtained between the partial pressure of oxygen and the ratio of $I_B^f/I_A^f$ (The concentration of dissolved oxygen gas in water is directly proportional to the partial pressure of oxygen in the mixed gas introduced [Henrys' law]). The ratio, $I_B^f/I_A^f$ remained unaffected by an intentional change of the light intensity from the excitation light source by means of a diaphragm.

INDUSTRIAL APPLICABILITY

As described above, this invention is directed to a method for optical detection of the concentration of a specific substance in a liquid or a gas by utilizing the quenching of a phosphor by the specific substance or a substance derived from the specific substance, which method is characterized by accomplishing the detection of the concentration of the specific substance by inducing the presence of both a first phosphor (A) quenched by the specific substance or a substance derived from the specific substance and a second phosphor (B) not substantially quenched by the specific substance or a substance derived from the specific substance, determining a light signal corresponding to the intensity ($I_A'$) of the emission from the first phosphor (A) and a light signal corresponding the intensity ($I_B'$) of emission from the second phosphor (B), and calculating the ratio between the light signals. The method, therefore, can determine the concentration of a specific substance in a liquid or a gas stably with high accuracy without being affected by such variable factors as variation in the light intensity of the excitation light source and variations in the physical conditions including bends in the optical fiber as the light guiding part, and the temperature of the ambient air. This invention, accordingly, brings about a great advance to the field of various types of analysis and determination such as the determination of concentrations of $O_2$ NO, $NO_2$, etc. in the air and the determination of concentrations of oxygen, nitrogen, hydrogen, carbon dioxide, chlorine, and argon dissolved in water, blood, and other aqueous media and to various industrial fields based on the analysis and determination.

Further, in the method of this invention for the optical determination of the concentration of a specific substance, when the ratio of the light signal corresponding to the intensity ($I_A'$) of emission from the first phosphor (A) and the light signal corresponding to the intensity ($I_B'$) of emission from the second phosphor (B) is determined with respect to at least two different known concentration of the specific substance for the purpose of calibration prior to the detection of the concentration of the specific substance, the determination of the concentration of the specific substance can be attained more easily. Particularly when the emission spectrum of the first phosphor (A) and the emission spectrum of the second phosphor (B) wall in mutually different wavelength regions, the determination can be attained with still higher accuracy with a simple configuration.

This invention is further directed to an apparatus comprising a sensor part formed of a layer containing a phosphor, an excitation light source for exciting the phosphor, a measuring part for detecting the intensity of emission, and a light guiding part for transmitting to the measuring part the light signal corresponding to the emission of the phosphor in the sensor part and effecting the optical determination of the concentration of a specific substance in a liquid or a gas by the utilization of the quenching of the phosphor by the specific substance or a substance derived from the specific substance, which apparatus is characterized by the fact that the sensor part contains at least two phosphors comprising at least one phosphor quenchable by the specific substance or a substance derived from the specific substance and at least one phosphor substantially unquenchable by the specific substance or a substance derived from the specific substance and the measuring part is provided with optical technical means for distinctly detecting the light signals corresponding to the intensities of emission of the phosphors. Thus, based on the method of this invention for the optical determination of the concentration of a specific substance mentioned above, the concentration of a specific substance in a liquid or a gas can be determined stably with high accuracy without being affected by variable factors.

Further, the determination of the concentration of a specific substance can be attained in a simpler configuration with higher accuracy when the sensor part contains at least two phosphors having their emission spectra in mutually different wavelength regions and comprising at least one phosphor quenchable by the specific substance or a substance derived from the specific substance and at least one phosphor substantially unquenchable by the specific substance or a substance derived from the specific substance, the sensor part is used commonly for the emissions of the phosphors, and the measuring part is provided with a spectroscope for spectrally dispersing the light signals led from the light guiding part into different wavelength components corresponding to the emissions of the phosphors, a photo-detector for converting the light signals in the wavelength components resulting from the spectral dispersion, and an arithmetic device for calculating the ratio between the light signal corresponding to the intensity of emission of the phosphor quenchable by the specific substance or a substance derived from the specific substance and the light signal corresponding to the intensity of emission of the phosphor substantially unquenchable by the specific substance or a substance derived from the specific substance in accordance with the electric signal obtained from the photo-detector. The influence of the variable factors can be kept down to a still lower level and the response is obtained more stably when the sensor part has the phosphor quenchable by the specific substance or a substance derived from the specific substance and the phosphor substantially unquenchable by the specific substance or a substance derived from the specific substance contained in one and the same reagent layer.

I claim:

1. A method for optical detection of the concentration of a specific substance in a liquid or a gas by utilizing the quenching of a phosphor by said specific substance or a substance derived from said specific substance, which method is characterized by accomplishing the detection of the concentration of said specific substance by inducing the presence of both a first phosphor (A) selected from the group consisting of tris(2,2'-bipyridine) ruthenium (II) complex, tris(1,10'-phenanthroline) ruthenium (II) complex, 1-pyrenebutyric acid and salts thereof, pyrene, aminopyrene, perylene, perylene dibutylate, and 2,7-dichlorofluorescein, quenched by the specific substance or a substance derived from said specific substance and a second phosphor (B) selected from the group consisting of proflavine sulfate, fluorescein, and eosin Y not substantially quenched by said specific substance or a substance derived from said specific substance, determining a light signal corresponding to the intensity ($I_A'$) of the emission from said first phosphor (A) and a light signal corresponding to the intensity ($I_B'$) of emission from said second phosphor (B), and calculating the ratio between said light signals.

2. A method according to claim 1, wherein the ratio between the light signal corresponding to the intensity ($I_A'$) of emission from said first phosphor (A) and the light signal corresponding to the intensity ($I_B'$) of emission from said second phosphor (B) is calculated relative to at least two different known concentrations of said specific substance for the purpose of calibration prior to said detection of the concentration of said specific substance.

3. A method according to claim 1 or claim 2, wherein the emission spectrum of said first phosphor (A) and the emission spectrum of said second phosphor (B) are present in mutually different wavelength regions.

4. A method according to claim 3, which is used for the determination of the concentration of oxygen.

5. A method according to any of claims 1 to 2, which is used for the determination of the concentration of oxygen.

6. An apparatus comprising a sensor part formed of a layer containing a phosphor, an excitation light source for exciting said phosphor, a measuring part for detecting the intensity of emission, and a light guiding part for transmitting to said measuring part the light signal corresponding to the emission of said phosphor in said sensor part and effecting the optical determination of the concentration of a specific substance in a liquid or a gas by the utilization of the quenching of said phosphor by said specific substance or a substance derived from said specific substance, which apparatus is characterized by said sensor part including at least two phosphors comprising at least one phosphor quenchable by said specific substance or a substance derived from said specific substance of tris(2,2'-bipyridine) ruthenium complex and at least one phosphor substantially unquenchable by said specific substance or a substance derived from said specific substance of proflavine sulfate and said measuring part being provided with optical technical means for distinctly detecting the light signals corresponding to the intensities of emission of said phosphors.

7. An apparatus according to claim 6, wherein said at least two phosphors have emission spectra in mutually different wavelength regions and include at least one phosphor quenchable by said specific substance or a substance derived from said specific substance and at least one phosphor substantially unquenchable by said specific substance or a substance derived from said specific substance.

8. An apparatus according to claim 7, wherein said light guiding part is used commonly for the emission of said phosphors and said measuring part comprises a spectroscope for spectrally dispersing the light signals led from said light guiding part into mutually different wavelength components corresponding to the emissions of said phosphors, a photo-detector for converting the light signals in said spectrally dispersed wavelength components into electric signals, and an arithmetic device for calculating the ratio between the light signal corresponding to the intensity of emission of the phosphor quenchable by said specific substance or a substance derived from said specific substance and the light signal corresponding to the intensity of emission of the phosphor substantially unquenchable by said specific substance or a substance derived from said specific substance in accordance with the electric signals obtained from said photo-detector.

9. An apparatus according to claim 7 or claim 8, wherein said sensor part has the phosphor quenchable by said specific substance or a substance derived from said specific substance and the phosphor substantially unquenchable by said specific substance or a substance derived from said specific substance contained in one and the same reagent layer.

10. A method for optical detection of the concentration of a specific substance in a liquid or a gas by utilizing the quenching of a phosphor by said specific substance or a substance derived from said specific substance, which method is characterized by accomplishing the detection of the concentration of said specific substance by inducing the presence of both a first phosphor (A) of tris(2,2'-bipyridine) ruthenium (II) complex quenched by the specific substance or a substance derived from said specific substance and a second phosphor (B) of proflavine sulfate not substantially quenched by said specific substance or a substance derived from said specific substance, determining a light signal corresponding to the intensity ($I_A'$) of the emission from said first phosphor (A) and a light signal corresponding to the intensity ($I_B'$) of emission from said second phosphor (B), and calculating the ratio between said light signals.

* * * * *